United States Patent [19]

Mohan et al.

[11] Patent Number: 5,438,148
[45] Date of Patent: Aug. 1, 1995

[54] **PROCESS FOR THE SYNTHESIS [R-(R*-,R*-)]-5-(3-CHLOROPHENYL-3-[2-(3,4-DIHYDROXYPHENYL)-1-METHYLETHYL]-2-OXAZOLIDINONE**

[75] Inventors: Arthur G. Mohan, Somerville; David M. Blum, Saddle River, both of N.J.

[73] Assignee: American Cyanamid Company, Wayne, N.J.

[21] Appl. No.: 309,303

[22] Filed: Sep. 20, 1994

[51] Int. Cl.⁶ ............................................ C07D 263/20
[52] U.S. Cl. .................................................... 548/229
[58] Field of Search ................ 548/229, 230, 231, 232

[56] References Cited

U.S. PATENT DOCUMENTS 5,061,727 10/1991 Bloom et al. ...................... 548/229

Primary Examiner—Donald G. Daus
Attorney, Agent, or Firm—H. G. Jackson; R. F. Boswell

[57] ABSTRACT

The invention is the simultaneous addition of boron tribromide and a solution of [R-(R*,R*)]-5-(3-chlorophenyl-3-[2-(3,4-dimethoxyphenyl)-1-methylethyl]-2-oxazolidinone in methylene chloride to methylene chloride while maintaining a constant ratio of 2.10:1.00 of boron tribromide to the substrate [R-(R*,R*)]-5-(3-chlorophenyl-3-[2-(3,4-dimethoxyphenyl)-1-methylethyl]-2-oxazolidinone at a temperature of $-5°$ C. to $10°$ C. gives [R-(R*,R*)]-5-(3-chlorophenyl-3-[2-(3,4-hydroxyoxyphenyl)-1-methylethyl]-2-oxazolidinone in an isolated yield of 86.7% and a purity of 98.7%.

1 Claim, No Drawings

PROCESS FOR THE SYNTHESIS [R-(R*,R*-)]-5-(3-CHLOROPHENYL-3-[2-(3,4-DIHYDROXYPHENYL)-1-METHYLETHYL]-2-OXAZOLIDINONE

BACKGROUND OF THE INVENTION

1. Field of Invention

The invention provides an improved process for the large scale production of [R-(R*,R*)]-5-(3-chlorophenyl-3-[2-(3,4-dihydroxyphenyl)-1-methylethyl]-2-oxazolidinone which is an intermediate useful in making compounds that have antidiabetic and/or antihyperglycemic and/or antiobesity properties in mammals and has the structural formula:

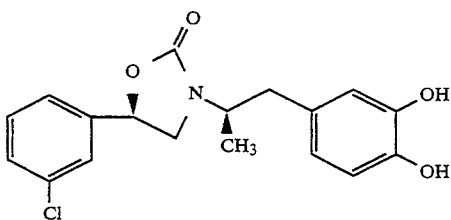

2. Description of the Prior Art

As described in copending application Ser. No. 164,524, filed Dec. 9, 1993 a process improvement for the preparation of [R-(R*,R*)]-5-(3-chlorophenyl-3-[2-(3,4-dihydroxyphenyl)-1-methylethyl]2-oxazolidinone which results in higher yields and purity as well as the elimination of a separate purification procedure is described which gives the desired product in a 75% overall yield and a purity of 80–90%.

U.S. Pat. No. 5,061,727 and copending application Ser. No. 164,524 do not teach the process of preparing [R-(R*,R*)]-5-(3-chlorophenyl-3-[2-(3,4-dihydroxyphenyl)-1-methylethyl]-2-oxazolidinone by the addition of a solution of [R-(R*,R*)]-5-(3-chlorophenyl-3-[2-(3,4-dimethoxyphenyl)-1-methylethyl]-2-oxazolidinone in methylene chloride to methylene chloride while simultaneously adding boron tribromide.

SUMMARY OF THE INVENTION

It has now been found that the simultaneous addition of boron tribromide and a solution of [R-(R*,R*)]-5-(3-chlorophenyl-3-[2-(3,4-dimethoxyphenyl)-1-methylethyl]-2-oxazolidinone in methylene chloride to methylene chloride while maintaining a constant ratio of 2.10:1.00 of boron tribromide to the substrate [R(R*,R*)]-5-(3-chlorophenyl-3-[2-(3,4-dimethoxyphenyl)-1-methylethyl]-2-oxazolidinone at a temperature of $-5°$ C. to 10° C. gives [R-(R*,R*)]-5-(3-chlorophenyl-3-[2-(3,4-hydroxyoxyphenyl)-1-methylethyl]-2-oxazolidinone in an isolated yield of 86.7% and a purity of 98.7%.

This process has the advantages of isolating the desired product in higher yield and purity than the cited literature procedures. In addition, this procedure is amenable to large scale manufacturing.

The process of the present invention is particularly effective at producing the desired product [R-(R*,R*)]-5-(3-chlorophenyl-3-[2-(3,4-dihydroxyphenyl)-1-methylethyl]-2-oxazolidinone essentially free from impurities in a reproducible manner on a large scale by permitting facile control of the highly exothermic reaction which results from treatment of [R-(R*,R*)]-5-(3-chlorophenyl-3-[2-(3,4-dimethoxyphenyl)-1-methylethyl]-2-oxazolidinone with boron tribromide.

DESCRIPTION OF THE PREFERRED EMBODIMENTS

In accordance with the present invention, there is provided a process as described in Scheme I in which [R-(R*,R*)]-5-(3-chlorophenyl-3-[2-(3,4-dimethoxyphenyl)-1-methylethyl]-2-oxazolidinone 1, prepared using the synthetic procedures described in U.S. Pat. No. 5,061,727, is dissolved in methylene chloride and added simultaneously along with boron tribromide to methylene chloride, under an inert gas while keeping the temperature at $-5°$ C. to 10° C. to give after quenching with methyl alcohol [R-(R*,R*)]-5-(3-chlorophenyl-3-[2-(3,4-dihydroxyphenyl)-1-methylethyl]-2-oxazolidinone 2. In accordance with the reaction conditions, the ratio of boron tribromide to [R-(R*,R*)]-5-(3-chlorophenyl-3-[2-(3,4-dimethoxyphenyl)-1-methylethyl]-2-oxazolidinone 1 is maintained constant at 2.10:1.00 during the simultaneous addition of the reactants. The progress of the reaction can be followed by taking aliquots of the reaction mixture, quenching with methyl alcohol and analyzing by high pressure liquid chromatography (HPLC).

After complete addition of both the boron tribromide and [R-(R* R*)]-5-(3-chlorophenyl-3-[2-(3,4-dimethoxyphenyl)-1-methylethyl]-2-oxazolidinone 1, the reaction mixture is maintained at 0°–5° C. for 10 minutes and methanol is slowly added at 0°–10° C. to destroy excess reagent. Evaporation of the solvents and adding water to the concentrate with water gives the desired [R(R*,R*)]-5-(3-chlorophenyl-3-[2-(3,4-dihydroxyphenyl)-1-methylethyl]-2-oxazolidinone 2 as a crystalline solid in high yield and purity.

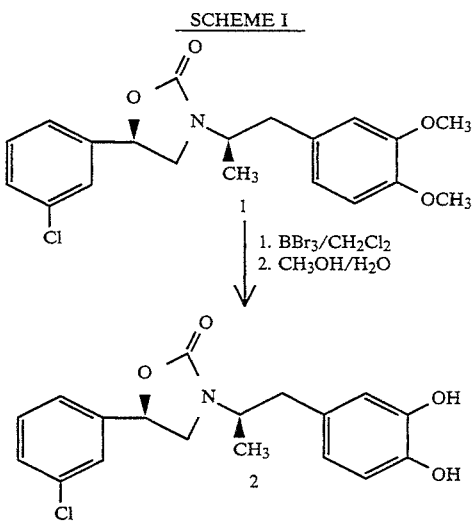

The reaction of boron tribromide with [R(R*,R*)]-5-(3-chlorophenyl)-3-[2-(3,4-dimethoxyphenyl)-1-methylethyl]-2-oxazolidinone 1 is highly exothermic and as a result the yield and purity of [R-(R*,R*)]-5-(3-chlorophenyl-3-[2-(3,4-dihydroxyphenyl)-1-methylethyl]-2-oxazolidinone 2 are very dependent on the mode of addition of the reagents. The proportion of by-products formed is strongly dependent on the manner in which the reactants are combined.

Additionally, we have found that the reproducibility of the formation of [R-(R*,R*)]-5-(3-chlorophenyl-3-[2-

(3,4-dihydroxyphenyl)-1-methylethyl]-2-oxazolidinone 2 can be seriously effected by the mode of addition of the reactants.

In a further aspect of this invention, simultaneous addition of boron tribromide and [R-(R*,R*)]-5-(3-chlorophenyl-3-[2-(3,4-dimethoxyphenyl)-1-methylethyl]-2-oxazolidinone 1 results in a reaction mixture which can be quenched with methyl alcohol at any time during the progress of the reaction and [R-(R*,R*)-]-5-(3-chlorophenyl-3-[2-(3,4-dihydroxyphenyl)-1-methylethyl]-2-oxazolidinone 2 isolated. This feature becomes an added advantage in large scale reactions in which there might be an equipment failure. [R-(R*,R*)]-5-(3-chlorophenyl-3-[2-(3,4-dihydroxyphenyl)-1-methylethyl]2-oxazolidinone 2 contains two chiral centers and is therefore a very expensive intermediate. Low yields seriously impact the cost of the final drug substance product.

The exotherm produced by the reaction of boron tribromide with [R-(R*,R*)]-5-(3-chlorophenyl-3-[2-(3,4-dimethoxyphenyl)-1-methylethyl]-2-oxazolidinone 1 is easily controlled by the simultaneous addition of both reactants. Careful control of the temperature, which is greatly assisted by the simultaneous addition minimizes byproduct formation and therefore highly pure product is recovered. The reaction can be terminated at any point during the addition and product recovered because the composition of the reaction product mixture remains relatively constant during the addition.

A further advantage of the simultaneous addition of boron tribromide and [R-(R*,R*)]-5-(3-chlorophenyl-3-[2-(3,4-dimethoxyphenyl)-1-methylethyl]-2-oxazolidinone 1 is that control of reaction temperature permits relatively simple scaleup to large reactors since cooling requirements are reduced. The option to stop the addition at any point in the progress of the reaction allows for greater flexibility in the manufacturing process and results in a process resistant to conditions in earlier methods.

The following non-limiting examples illustrate the process of the present invention.

Example 1

[R-(R*,R*)]-5-(3-chlorophenyl-3-[2-(3,4-dihydroxyphenyl)-1-methylethyl]-2-oxazolidinone A 100 mL 4 neck round bottom flask containing 15 mL of dichloromethane is cooled to 1° C. under a nitrogen atmosphere. A solution of [R-(R*,R*)]-5-(3-chlorophenyl-3-[2-(3,4-dimethoxyphenyl)-1-methylethyl]-2-oxazolidinone (4.00 g, 0.0106 mol) in 9.0 mL of dichloromethane solution is added at a constant rate over 10 minutes from a syringe pump using a 10 mL gas-tight. syringe fitted with a Teflon ® needle. At the same time boron tribromide (2.11 mL, 5.59 g, 0.0223 mol) is added in a similar manner from a 2.5 mL gas-tight syringe fitted with a Teflon ® needle. The temperature is maintained at 1° to 4° C. during the addition and the reaction mixture held for 10 minutes after completion of the addition (final temperature was −1° C.). At this point HPLC analysis of an aliquot of the reaction mixture (quenched into methanol) indicates none of the starting material is present and only traces of the two monomethyl ether isomers detected. The major component is the expected [R-(R*,R*)]-5-(3-chlorophenyl-3-[2-(3,4-dihydroxyphenyl)-1-methylethyl]-2-oxazolidinone. The reaction mixture is quenched by the addition of methanol (40 mL). The methanol is added initially very slowly in order to control the exotherm and maintain the temperature at 0° to 10° C. After quenching, the mixture is concentrated by distillation under reduced pressure on a rotary evaporator leaving 9.5 g of a colorless oil. Water (40 mL) is added to precipitate the product and the resulting slurry is stirred overnight at ambient temperature. The product is recovered by filtration and washed twice with 15 mL portions of water. Drying in a fluid bed drier at 60° C. affords 3.21 g (86.7% yield) of the desired product. The purity is 98.7% (HPLC area %).

We claim:

1. A process for producing a compound of the formula:

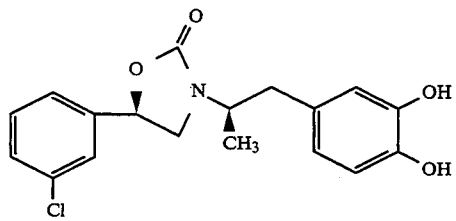

which comprises:
a) adding a methylene chloride solution of [R-(R*,R*)]-5-(3-chlorophenyl-3-[2-(3,4-dimethoxyphenyl)-1-methylethyl]-2-oxazolidinone to methylene chloride while simultaneously adding boron tribromide at about −5° to about 10° C. under inert gas at a rate so the ratio of boron tribromide to substrate is 2.10:1.00;
b) quenching the reaction mixture with methyl alcohol at about −5° to about 10° C.;
c) concentrating the reaction mixture by distillation of the methylene chloride and a portion of methyl alcohol;
d) adding water to the reaction mixture;
e) collecting the product by filtration and drying.

* * * * *